US00PP13097P2

(12) United States Plant Patent
Trees

(10) Patent No.: US PP13,097 P2
(45) Date of Patent: Oct. 22, 2002

(54) ANTIRRHINUM PLANT NAMED 'BALUMDEPUR'

(75) Inventor: Scott C. Trees, Shell Beach, CA (US)

(73) Assignee: Ball FloraPlant, a division of Ball Horticultural Corporation, West Chicago, IL (US)

( * ) Notice: Subject to any disclaimer, the term of this patent is extended or adjusted under 35 U.S.C. 154(b) by 0 days.

(21) Appl. No.: 09/808,286

(22) Filed: Mar. 14, 2001

(51) Int. Cl.[7] ..... A01H 5/00
(52) U.S. Cl. ..... Plt./322
(58) Field of Search ..... Plt./322

*Primary Examiner*—Bruce R. Campell
*Assistant Examiner*—June Hwu
(74) *Attorney, Agent, or Firm*—Wood, Phillips, Katz, Clark & Mortimer

(57) ABSTRACT

A new and distinct Antirrhinum plant named Balumdepur characterized by its trailing habit and deep purple flowers.

2 Drawing Sheets

LATIN NAME OF THE GENUS AND SPECIES OF PLANT CLAIMED

*Antirrhinum majus.*

VARIETY DENOMINATION

Balumdepur.

BACKGROUND OF THE INVENTION

The present invention comprises a new and distinct Antirrhinum plant, hereinafter referred to by the cultivar name Balumdepur. This new cultivar was developed by the inventor through a controlled breeding program during August 1997 at Arroyo Grande, Calif. The objective of the breeding program was the development of Antirrhinum cultivars with trailing mounded habit, continuous flowering, excellent basal branching and small, dark green foliage.

The female parent of Balumdepur was Lampion Purple (U.S. Plant Pat. No. 9,986) which is characterised by its trailing habit, dark lavender flowers and hirsute dark green foliage. The male parent of Balumdepur was Lampion Yellow (U.S. Plant Pat. No. 9,985) which is characterised by its trailing habit, dark yellow flowers and hirsute dark green foliage. The resulting seed was collected and germinated. From the flowering progeny, a plant was selected in April 1998 and initially designated 94-8.

Asexual reproduction of the new cultivar by terminal cuttings taken at Arroyo Grande, Calif., U.S.A. has demonstrated that the characteristics of the new cultivar as herein described are firmly fixed and retained through successive generations of such asexual propagation.

SUMMARY OF THE INVENTION

It was found that the cultivar of the present invention:

(a) Exhibits a trailing habit, (b) Forms abundant dark purple flowers and (c) Exhibits dark green foliage.

When the new cultivar of the present invention is compared to Lampion Purple it is found that the new cultivar exhibits leaves of a different shape and color and flowers slightly smaller and darker purple in color. When compared to Chandelier Primrose Vein (not patented in the United States) the new cultivar exhibits leaves of a different shape, color and texture and flowers of a different color as detailed in TABLE 1.

BRIEF DESCRIPTION OF THE PHOTOGRAPHS

The accompanying photographs show as nearly true as it is reasonably possible to make the same in color illustrations of this type, typical flower and foliage characteristics of the new cultivar.

The first photograph comprises a view of the growth habit of Balumdepur in a pot containing three plants.

The second photograph comprises a close-up view of typical flowers and foliage of Balumdepur. Colors appear darker than the actual flower and foliage colors.

The plants were grown in a greenhouse at West Chicago, Ill., USA.

DETAILED BOTANICAL DESCRIPTION

The Balumdepur cultivar has not been observed under all possible environmental conditions to date. Accordingly, it is possible that the phenotype may vary somewhat with variations in the environment, such as temperature, light intensity and day length.

The chart used in the identification of colors described herein is The R.H.S. Colour Chart of The Royal Horticultural Society, London, England. The color values were determined on Sep. 26, 2000 in West Chicago, Ill. The readings were taken between 11:00 and 11:45 p.m. under natural light conditions. The plants were produced from cuttings taken from stock plants and grown for ten (10) weeks in a double poly carbonate covered greenhouse under conditions comparable to those used in commercial practice while utilizing a soilless growth medium and maintaining temperatures of approximately 72° F. during the day and approximately 65° F. during the night.

Classification:

*Botanical.*—*Antirrhinum majus* cultivar Balumdepur.

*Commercial.*—Trailing Snapdragon.

Propagation:

*Type cutting.*—Terminal tip.

*Time to initiate roots.*—Approximately 10–14 days with the shorter times generally being experienced in the summer and the longer times in the winter.

*Root description.*—Fibrous, branching.

Plant description:

*General appearance and form.*—Mounded and trailing.

*Plant length (from top of plant plane to lower flowers)*.—Approximately 23 cm.

*Plant width.*—Approximately 35.5 cm.

*Branching habit.*—Freely branching. Pinching encourages branching.

*Stem.*—Diameter at lowest node approximately 2 mm, closest to 146D in color, densely covered with medium length, soft hairs.

*Internode length.*—Approximately 1 cm.

Foliage description:

*Shape.*—Ovate, acute apex, attenuate base, entire margin.

*Arrangement.*—Opposite.

*Venation pattern.*—Arcuate.

*Texture.*—Upper surface is smooth, lower surface is densely covered with short, soft hairs.

*Color of mature foliage.*—Upper surface is darker than 146A with venation of 146B, lower surface is closest to 146B with venation of 146B.

*Size of mature leave.*—Approximately 2.3 cm in length, approximately 1.2 cm in width.

*Petiole.*—Length is approximately 4 mm, diameter is approximately 1 mm, color is 146B, surface is covered with short soft hairs.

Flower description:

*Flowering habit.*—Balumdepur is freely flowering under outdoor growing conditions with substantially continuous blooming from spring until fall.

*Flower arrangement.*—Terminal racemes.

*Peduncle.*—Length is approximately 8 mm, diameter is approximately 1 mm; color is closest to 146D.

*Flower.*—Bilabiate, approximately 3.2 cm in length. Lip texture smooth, margin entire and somewhat undulating. Upper lip is 2 parted, approximately 1.5 cm in length, 1.4 cm in width, 71A at edge, 72A at base. Lower lip is 3 parted, approximately 1.5 cm long, 1.6 cm wide, 71A at edge, 72A with two areas of 13A where lip meets palate. Lower palate is 155D with hairs of 155D along outer edges and hairs of 8B in center. Inside throat is 155D with venation of 60B and a few hairs of 8B.

*Flower bud.*—Length is approximately 2.6 cm, width is approximately 1.2 cm, color 71A.

*Calyx.*—5 sepals, approximately 7 mm in length, approximately 3 mm in width, acute apex, between 143A and 144A in color, densely covered with short hairs.

*Reproductive organs.*—Androecium: 4 stamens, 2 are approximately 1.7 cm and 2 are approximately 2 cm in length, closest to 155D in color. Anthers approximately 2 mm in length, 164C in color. Pollen color is closest to 19A. Gynoecium: One pistil. Stigma length is approximately 2 mm, color is 144B. Style length is approximately 1.4 cm, color is 72B. Ovary is 2 mm in diameter, pubescent and 145D in color.

Seed production: Seed production has not been observed.

Disease resistance: Resistance to pathogens has not been observed.

TABLE 1

| CHARACTERISTIC | BALUMDEPUR | LAMPION PURPLE | CHANDELIER PRIMROSE VEIN |
|---|---|---|---|
| MATURE LEAF LENGTH × WIDTH-CM | 2.3 × 1.2 | 3 × 1.5 | 1.2 × 1 |
| COLOR OF UPPER SURFACE OF MATURE FOLIAGE | DARKER THAN 146A | 147A | 189A |
| COLOR OF LOWER SURFACE OF MATURE FOLIAGE | 146B | 137C | 191A |
| LEAF SHAPE | NARROW ELLIPTIC | ELLIPTIC | OVAL |
| FLOWER COLOR-UPPER LIP | 71A AT EDGE, 72A AT BASE | 72B | 155D WITH VEINS OF 70A |
| FLOWER COLOR-LOWER LIP | 71A AT EDGE, 72A WITH 2 AREAS OF 13A WHERE RIM MEETS PALATE | 71A WITH TWO AREAS OF 13A WHERE RIM MEETS PALATE | 155D WITH VEINS OF 69A |
| FLOWER SIZE-LENGTH × WIDTH-CM | 3.2 × 1.6 | 4.2 × 1.8 | 3.1 × 1.3 |

I claim:

1. A new and distinct cultivar of Antirrhinum plant named Balumdepur substantially as herein shown and described, which:

(a) Exhibits a trailing growth habit, (b) Forms abundant deep purple flowers and (c) Exhibits dark green foliage.

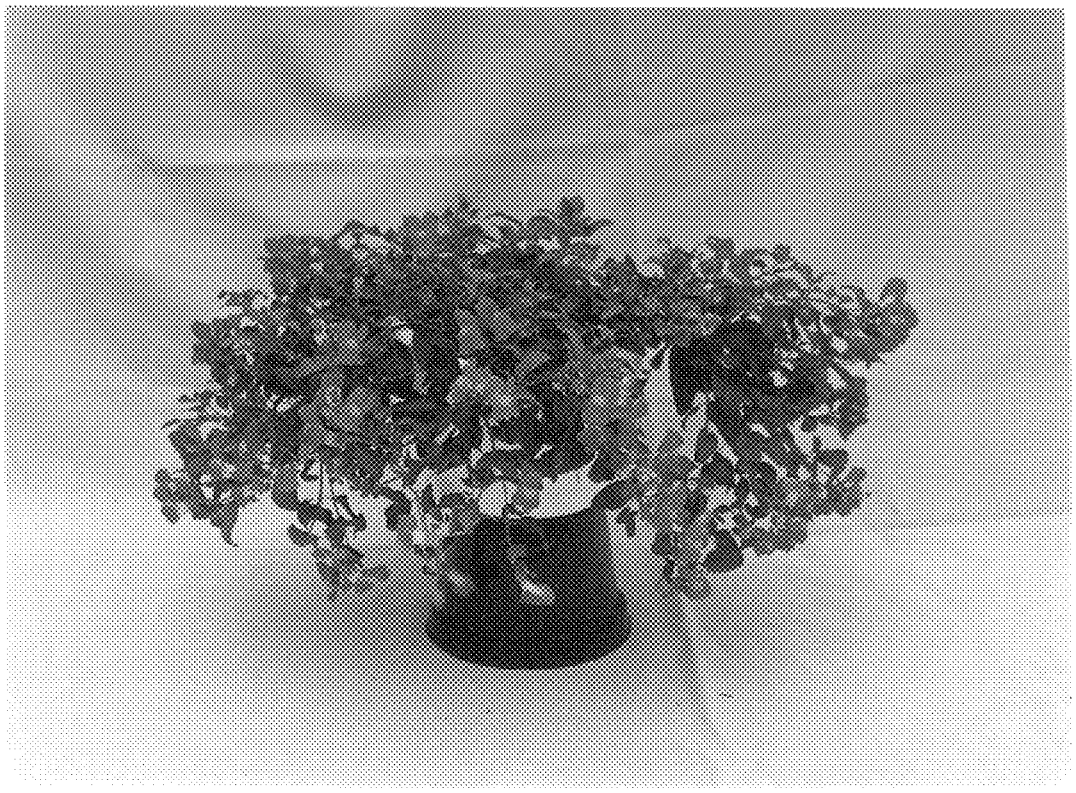

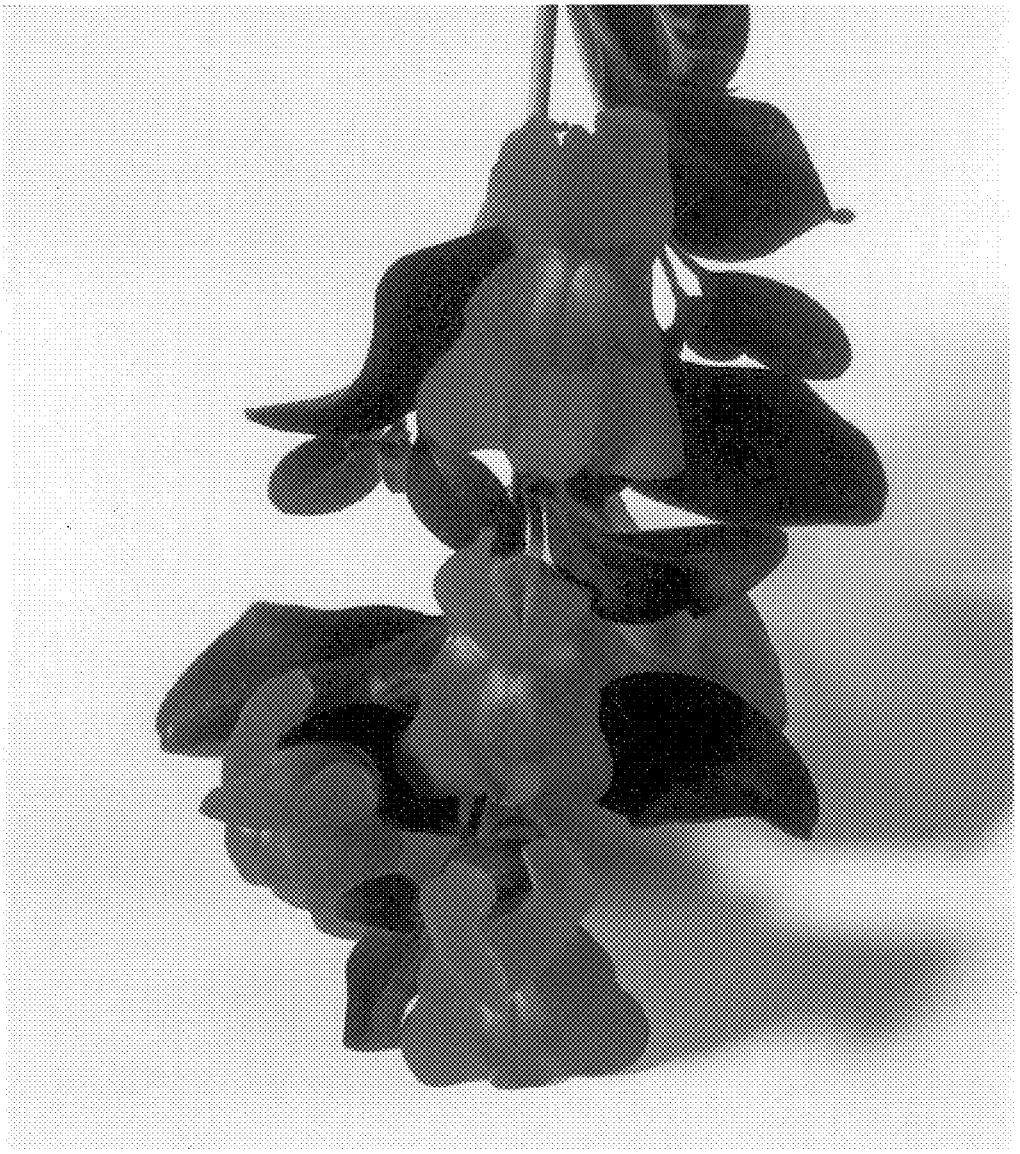

* * * * *